United States Patent [19]

Pastrone et al.

[11] Patent Number: 4,927,411
[45] Date of Patent: May 22, 1990

[54] DRIVE MECHANISM FOR DISPOSABLE FLUID INFUSION PUMPING CASSETTE

[75] Inventors: John Pastrone, Los Gatos; Edward Laenen, Palo Alto, both of Calif.

[73] Assignee: Abbott Laboratories, Abbott Park, Ill.

[21] Appl. No.: 45,924

[22] Filed: May 1, 1987

[51] Int. Cl.$^5$ .............................................. A61M 31/00
[52] U.S. Cl. ..................................... 604/65; 604/153; 251/251
[58] Field of Search ........................ 604/50, 65, 66, 67, 604/152, 153, 245, 246, 247, 248, 249; 128/DIG. 12; 251/213, 231, 235, 236, 251, 253, 254, 259, 260, 261

[56] References Cited

U.S. PATENT DOCUMENTS

| | | |
|---|---|---|
| 2,308,974 | 1/1943 | Harper . |
| 3,620,650 | 11/1971 | Shaw . |
| 4,142,524 | 3/1979 | Jassawalla . |
| 4,165,208 | 8/1979 | Lundquist . |
| 4,181,245 | 1/1980 | Garrett et al. . |
| 4,199,307 | 4/1980 | Jassawalla . |
| 4,273,121 | 6/1981 | Jassawalla . |
| 4,303,376 | 12/1981 | Siekmann . |
| 4,336,800 | 6/1982 | Pastrone . |
| 4,381,005 | 4/1983 | Bujan . |
| 4,398,908 | 8/1983 | Siposs . |
| 4,453,931 | 6/1984 | Pastrone . |
| 4,457,753 | 7/1984 | Pastrone . |
| 4,468,222 | 8/1984 | Lundquist . |
| 4,470,758 | 9/1984 | Pazemenas . |
| 4,474,309 | 10/1984 | Solomon . |

Primary Examiner—John D. Yasko
Attorney, Agent, or Firm—Harry G. Thibault; Robert E. Wexler

[57] ABSTRACT

A disposable fluid infusion pumping chamber cassette comprises a sandwich type construction which lends itself to a multiplicity of control and monitoring functions including pressure monitoring, air bubble detection monitoring, adaption to multiple inputs, and leak detection monitoring, the cassette includes a rigid face member and a rigid back member having an elastomeric diaphragm positioned therebetween, provides for the transmission of fluid from one end of the cassette to the other, and includes an enlarged recess portion forming the pumping chamber, with exposed openings in the face member opposite the pumping chamber to permit the passage of a plunger and opposed openings adjacent the fluid passage to permit the selective actuation of valving members therein, with a flow control member mounted upon the face member adjacent the passage between the pumping chamber and fluid outlet thereof, which is utilized to either open the passage to free flow of fluid or to block it off completely.

13 Claims, 9 Drawing Sheets

DRIVE MECHANISM FOR DISPOSABLE FLUID INFUSION PUMPING CASSETTE

BACKGROUND OF THE INVENTION

This invention relates to a disposable cassette having a pumping chamber therein and with a controlled positive displacing pump driving apparatus for use with the cassette, for performing intravenous or intra-arterial infusions. More particularly, it pertains to disposable cassettes which include an exposed flexible diaphragm forming one wall of the pump chamber and adapted to be engaged by a plunger or piston member driven and controlled by the driver apparatus to pump fluid through the cassette.

In recent years there has been a increasing use of positive displacement fluid infusion pumping devices for delivery fluids intravenously or intra-arterially to patients in hospitals or other patient care locations. These have to a large extent replaced the time-honored gravity flow control systems, primarily due to their much greater accuracy in delivery rates and dosages, the relative sophistication in permitting a flexible and controlled feed from multiple liquid sources, and particularly their ability to control with precision the amount of dangerous drugs delivered to a patient over a given period of time.

A typical positive displacement infusion pump system includes a pump driver device and a disposable cassette. The disposable cassette, which is adapted to be used only for a single patient and for one fluid delivery cycle, is typically a small plastic unit having an inlet and an outlet respectively connected through flexible tubing to the fluid supply container and to the patient receiving the infusion. The cassette includes a pumping chamber with the flow of fluid through the chamber being controlled by a plunger or piston activated in a controlled manner by the driver device. For example, the cassette chamber may have one wall thereof formed by a flexible diaphragm which is reciprocated by the plunger in the driver to cause fluid to flow. The pump driver device includes the plunger or piston for controlling the flow of fluid into and out of the pumping chamber in the cassette, and it also includes control mechanisms to assure that the fluid is delivered to the patient at a preset rate, in a pre-determined manner, and only for a particular pre-selected time or total dosage. The pump driver device may also include pressure sensing and other liquid flow monitoring devices as well as valving members for opening and closing various passages in the cassette including the inlet and outlet passages of the pumping chamber.

SUMMARY OF THE INVENTION

The disposable fluid infusion pumping chamber cassette of the present invention may be readily and relatively inexpensively manufactured in three pieces. The sandwich type construction of the cassette also lends itself to a multiplicity of control and monitoring functions including, for example, pressure monitoring, air bubble detection monitoring, adaption to multiple inputs, and leak detection monitoring, all of which functions can be performed without modifying the basic cassette structure.

Briefly, the cassette of the present invention includes a rigid face member and a rigid back member having an elastomeric diaphragm positioned therebetween. The back member is configured to provide for the transmission of fluid from one end of the cassette to the other and includes an enlarged recess portion forming the pumping chamber. The face member includes exposed openings opposite the pumping chamber to permit the passage of a plunger and opposed openings adjacent the fluid passage to permit the selective actuation of valving members therein. Finally, a flow control member is mounted upon the face member adjacent the passage between the pumping chamber and fluid outlet thereof, which flow control member can be utilized to either open the passage to free flow of fluid or to block it off completely.

BRIEF DESCRIPTION OF THE DRAWING

FIGS. 22 A-C are schematic views of various positions of the positioning flag for the cassette inlet and outlet actuator drive assembly;

FIGS. 23 A-C are schematic views of various positions of the positioning flag for the pumping chamber inlet and outlet actuator drive assembly.

DETAILED DESCRIPTION OF THE PREFERRED EMBODIMENT

I. Pumping Cassette

Figures 1, 2, 3, 4:
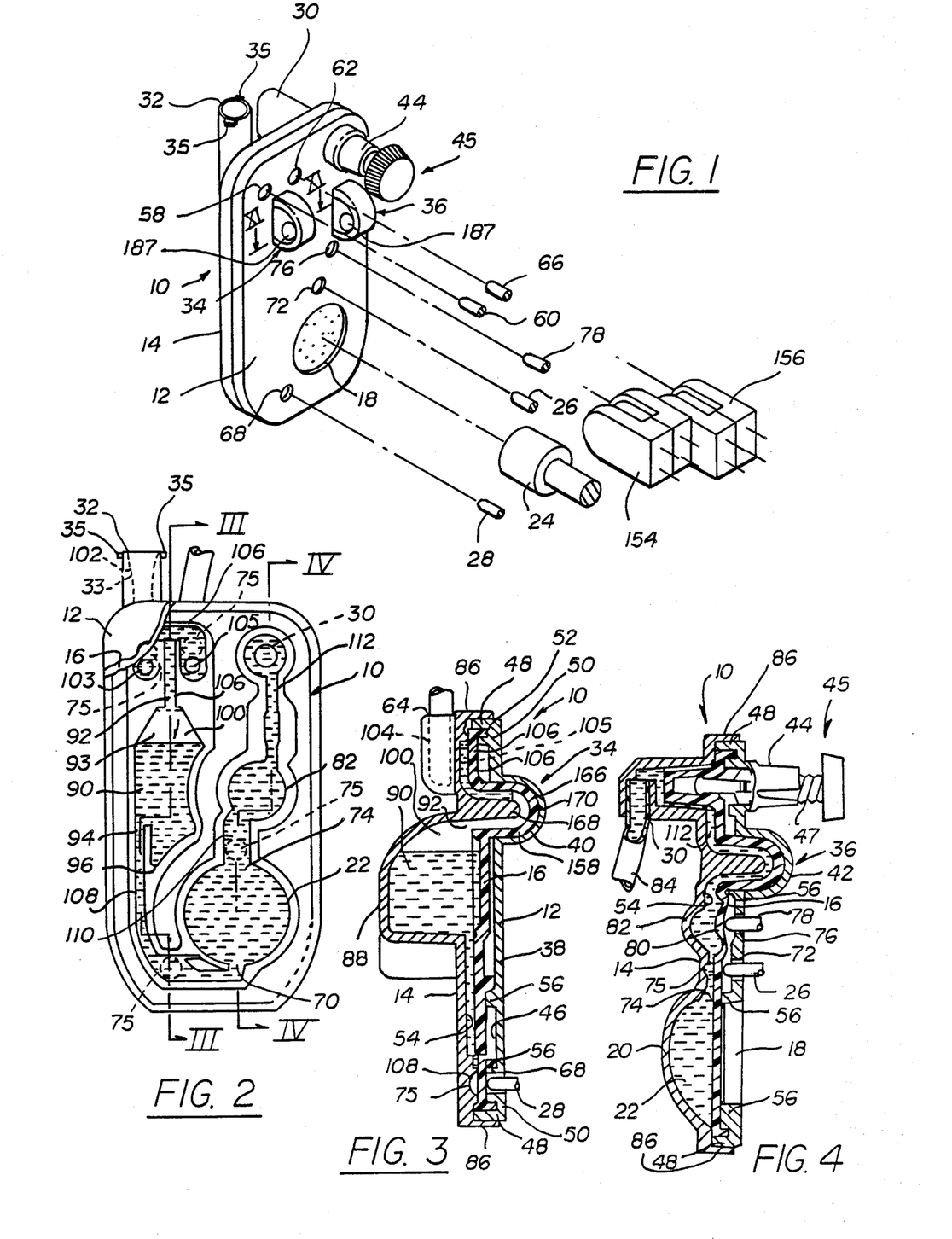
FIG. 1 is a perspective view of a pumping cassette of the present invention along with selected portions of a driver to drive the pump cassette.
FIG. 2 is a plan view of the cassette of the present invention with one face broken away.
FIG. 3 is a cross section taken along the plane of line 3—3, of FIG. 2.
FIG. 4 is a cross section taken along the plane of line 4—4 of FIG. 2.

A pumping cassette 10 of the present invention is illustrated in FIGS. 1-4. It includes a rigid face member 12 and a rigid back member 14 with an elastomeric member 16 positioned between. Face member 12 has plunger opening 18 with elastomeric member 16 extending across the opening. Behind plunger opening 18 in back member 14 is an enlarged recess 20, which forms a pumping chamber 22. To pump fluid from chamber 22, a plunger 24 (FIG. 1) reciprocates into and out of opening 18 urging the diaphragm across opening 18 into and out of chamber 22. As plunger 24 is urged against the diaphragm, a pumping chamber outlet valve actuator 26 is opened while the pumping chamber inlet valve actuator 28 is closed so that fluid is forced from chamber 22 out of the cassette outlet 30. After the plunger has expelled a measured amount of fluid from pumping chamber 22, valve actuator 26 closes, and valve actuator 28 opens. Plunger 24 is withdrawn from chamber 22, whereupon liquid is drawn into pumping chamber 22 from primary cassette inlets 64 (FIG. 3). As will be explained in greater detail below, cassette 10 further includes air-in-line detection means 34 in the fluid path between primary cassette inlet 64 and pumping chamber 22, and air-in-line detection means 36 the fluid path between pumping chamber 22 and cassette outlet 30. Detection means 34 and 36 can be used to detect whether air is being drawn into the system and whether the valves in the cassette are working properly to prevent fluid from flowing at an uncontrolled rate through the cassette.

Face member 12 is preferably molded from rigid plastic such as polycarbonate. Face member 12 has a generally flat exterior face 38-flat with the exception of a semi circular guard member 40 for air-in-line detection means 34, a semi-circular guard member 42 for air-in-line detection means 36, and a cylindrical housing 44 for a flow control regulator 46. The interior face 46 of face member 12 is flanged, having a peripheral pair of flanges 48 and 50, which extend completely around the peripheral face member 12 toward back member 14. Flanges 48 and 50 are spaced from each other and receive between them a peripheral flange 52 of the elastomeric member 16.

Interior face 46 of face member 12 also includes flanges 56 on either side of the fluid path through cassette 12 in the outline of the fluid path (see FIG. 2) which pinch or retain elastomeric member 16 against the interior face 54 of back member 14 to prevent fluid from leaking out of the fluid path into other areas within cassette, not part of the fluid path. The details of the fluid path are described below.

Face member 2 also includes valve actuator openings. A primary cassette inlet valve actuator opening 62 is located adjacent primary cassette inlet 64 to allow a finger-like primary inlet actuator 66 to regulate the flow of fluid into the cassette. Inlet actuator 66 extends through opening 62 and is selectively moved inwardly of opening 62 to urge a portion of the elastomeric member 16 across the fluid path and against the inside surface of back member 14 to block the flow of fluid into cassette 10 from inlet 64. The inlet actuator opening 62 and the portion of elastomeric member 16 adjacent opening 62 form a primary cassette inlet valve.

A secondary cassette inlet actuator opening 58 is located adjacent a secondary cassette inlet 32. Opening 58 permits a secondary inlet actuator 60 to urge a portion of elastomeric member 16 across the fluid path and against the inside surface of back member 14 so as to block the flow of fluid from secondary inlet opening 32 into the cassette. Inlet actuator opening 58 and the portion of elastomeric member 16 adjacent opening 58 form a secondary cassette inlet valve. Primary inlet 64 and secondary inlet 32 can be connected to primary and secondary sources of fluid. Actuators 66 and 60 are used to select which fluid is pumped by cassette 10 at any given moment, if two liquids are being pumped to the patient at a given time. Alternatively, if one liquid is being administered, the liquid container is connected to primarily inlet 64, and the primary cassette inlet valve is opened while the secondary cassette inlet valve is closed during fluid administration. The mechanism used to drive inlet actuators 66 and 60 is described below.

A pump chamber inlet actuator opening 68 (FIGS. 1 and 3) is located upstream of the fluid path leading to pump chamber inlet 70 (FIG. 2) which is positioned at the bottom of pump chamber 22. Actuator opening 68 allows actuator 28 to urge a portion of elastomeric member 16 adjacent opening 68 across the fluid path leading into pump chamber 22 to block the flow of fluid into pump chamber 22 from cassette inlets 32 and 62 and to block the flow of fluid from pump chamber 22 back through cassette inlets 32 or 62. Pump chamber inlet actuator opening 68 and the portion of elastomeric member 16 adjacent opening 68 form a pump chamber inlet valve.

A pump chamber outlet actuator opening 72 (FIGS. 1 and 4) is provided through face member 12 to allow a pump chamber outlet actuator 26 to urge a portion of elastomeric member 16 across the fluid path leading from pump chamber outlet 74 (FIGS. 2 and 4) to selectively block the flow of fluid from chamber 22 out of outlet 74. Opening 72 and the portion of elastomeric member 16 adjacent opening 72 form a pump chamber outlet valve.

As shown in connection with inlet actuator 28 in FIG. 3, back member 14 has a concave, circular valve seat 75 opposite each actuator opening 58, 62, 68, and 72. Each valve actuator 26, 28, 60, and 66 has a rounded end so that when a valve actuator is urged inwardly through an actuator opening, a portion of the elastomeric member 16 will be urged into a valve seat 75, insuring that flow is blocked when an actuator is actuated.

Face member 12 further includes a pressure sensor opening 76 which allows a rod-like extension 78 of a pressure sensor 77 (FIG. 14) associated with the pump cassette driver (not shown) to contact a pressure detection section 80 (FIG. 4) of elastomeric member 16 positioned over a pressure chamber 82 in back member 14. Thus, the pressure of fluid being pumped from pumping chamber 22 can be monitored. If the pressure is excessive, it may be a sign that the needle in the patient s arm attached to the end of a tube 84 connected to outlet 30 has been blocked. This pressure detection system can also be employed to check the integrity of the valving of the pump chamber 22 at its inlet and outlet as will be described below. Finally, this pressure detection system can be used to monitor the patient's blood pressure, as will be discussed below.

Back member 14 is also made of a rigid, polymeric material preferably polycarbonate. Back member 14 includes a peripheral flange 86 (FIGS. 3 and 4) in which peripheral flange 48 of face member 12 nests. Flanges 48 and 86 are secured together in a sealed fashion by welding, gluing and the like.

As indicated previously, back member 14 includes cassette inlets 64 and 32. Secondary inlet 32 is provided with a luer taper 33 and thread-like flanges 35 to accept a luer cap for capping inlet 32 when only one liquid is to be pumped, or connecting to a luer lock tubing connector when two liquids are to be pumped. Back member 14 also includes a recess 20 which forms pumping chamber 22 and a recess 82 which forms a pressure detection chamber. A reservoir recess 88 is also provided in back member 14 to form a reservoir 90 (FIGS. 2 and 3) when the unit is assembled.

Reservoir 90 has an inlet 92 at the top of reservoir 90, and an outlet 94 above the bottom 96 of reservoir 93. When the cassette is initially primed with liquid prior to pumping, the cassette is inverted from the position shown in FIG. 2 so that the air in the fluid path between cassette inlets 32 and 62 and pumping chamber inlet 70 is displaced with liquid with the exception of the air trapped between the bottom 96 and outlet 94 of drip chamber 90. This trapped volume of air 93 rises to the top of drip chamber 90 when the cassette is returned to its upright pumping position shown in FIGS. 2 through 4. The function of trapped air 93 will be explained below.

Figure 10:
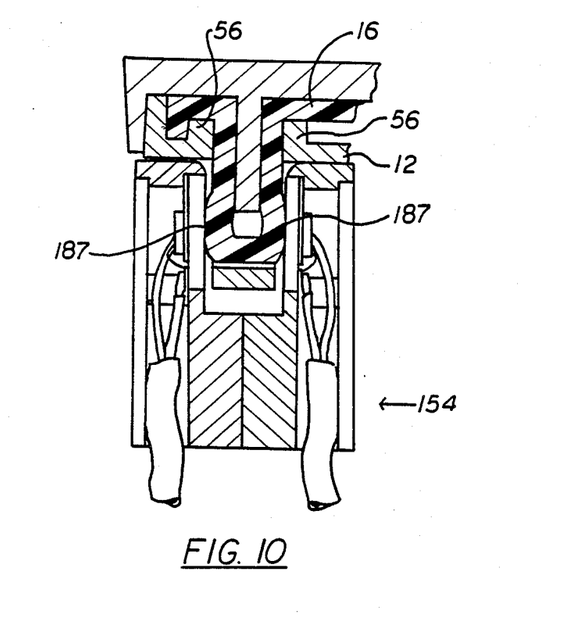
FIG. 10 illustrates the air-in-line detection system of the cassette of the present invention.

Reservoir 90, pressure detection chamber 82, and pumping chamber 22 form portions of the fluid path between cassette inlets 32 and 62 and cassette outlet 30. The remaining portions of the fluid path are also formed on the inside surface 54 of back member 14. An inlet passage 104 (FIGS. 3 and 17) connects primary inlet 64 to an opening 105 (FIG. 3) inside of the cassette. Secondary inlet 32 is connected with an opening 103 in cassette 10 by an inlet passage 102 (FIGS. 2 and 10). Fluid from openings 103 and 105 combine in a channel 106 (FIGS. 2 and 3), formed between membrane 16 and back member 14 and flows into air-in-line detection means 34, which will be described in detail below. From air-in-line detection means 34, the fluid flows through reservoir inlet 92 into reservoir 90. From reservoir 90, the fluid enters a passage 108, valved at its lower end by pump chamber inlet valve actuator 28, into pumping chamber 22 through pumping chamber inlet 70. A short channel 110 valved by pump chamber outlet valve actuator 28 connects pump chamber outlet 74 to pressure detection chamber 82. The fluid flows through pressure detection chamber 82 into air-in-line detection means 36. From air-in-line detection means 36, fluid flows through a channel 112 which leads to flow control regulator 45.

Before flowing out of cassette outlet 30, the fluid flows through flow control regulator 45, disclosed in copending U.S. application Ser. No. 856,723 filed Apr. 25, 1986 entitled Liquid Flow Regulator by Giovanni Pastrone, which is a continuation-in-part of application Ser. No. 776,399 filed Sept. 16, 1985, which is a continuation-in-part of application Ser. No. 811,262, now a U.S. Pat. No. 4,552,336, entitled "Liquid Flow Regulator". The disclosures of these applications and patent are hereby incorporated herein by reference.

As disclosed in U.S. patent application No. 856,723, flow regulator 45 includes a plunger 47 and a cylindrical housing 44. Plunger 47 and housing 44 are configured to allow plunger 47 to be threaded inwardly of housing 44 to reduce or prevent the flow of fluid through regulator 45, or to be threaded outwardly of cylindrical housing 44 to increase or allow fluid to flow through regulator 45. With this controlled inward and outward threading of plunger 47 in housing 44, plunger 47 can be used to regulate manually the flow of fluid through the cassette when the cassette is not mounted in a driver, permitting regulated gravity flow of fluid from the I.V. solution container to the patient. Thus, when the patient is being transported, say in an ambulance, an I.V. set with the cassette of the present invention can be employed without the cassette driver to regulate flow of I.V. solution to the patient. But, when the patient arrives at the hospital, the cassette can be mounted on a cassette driver described in more detail below to regulate the flow of fluid more precisely than with the manual gravity method described above.

Also as described in more detail in the aforesaid U.S. patent application No. 856,723, flow regulator plunger 47 is adapted to be pushed inwardly into or pulled outwardly of cylindrical housing 44 to allow rapid movement between on and off positions.

II. Flow Regulator Shutoff Assembly

The cassette driver mechanism includes a flow regulator shutoff assembly 114 (FIGS. 5-9) to pull plunger 47 rapidly outward into the open position when the cassette is mounted in the driver, and to push plunger 47 inward into the "off" position when the cassette is removed from the driver. Flow regulator shutoff assembly 114 includes a gripper bracket 116 having two downwardly depending arms 118, 118' joined a bight portion 120 at their upper ends. Pivotally mounted between arms 118, 118' is a chevron-shaped depressor member 122. Depressor member 122 is pivotally mounted to and between arms 122 by a pin 124. Depressor member 122 is also pivotally mounted about a pin 126 which is fixedly mounted on the chassis 128 of the cassette driver assembly.

Also mounted between arms 118 and 118' is a cam 130 which is fixedly mounted on a rotatable shaft 132. Cam 130 has cam surfaces 134 and 134' which engage corresponding cam surfaces 136 and 136' on the inside of depressor member 122. Cam 130 further includes a driving pin 138 which extends through 130 to engage the lower ends of arms 118 and 118' in a manner to be described below.

Flow regulator shutoff assembly 114 further includes a slotted pivot arm 140 which is fixedly secure to rotatable shaft 132 which in turn is mounted on chassis 128 so as to allow shaft 132 to rotate freely about its longitudinal axis but to restrain it from translational movement in horizontal or vertical directions. Pivot arm 140, therefore, will pivot in tandem with cam 130.

Pivot arm 140 has a slot 142 in which a roller 144 is free to slide. Roller 144 is mounted on the driver door 146 in which cassette 10 is mounted when in the driver. The driver door 146 is pivotally mounted on a pin 148 which is also fixedly secure to chassis 128 of the driver.

Figure 5:
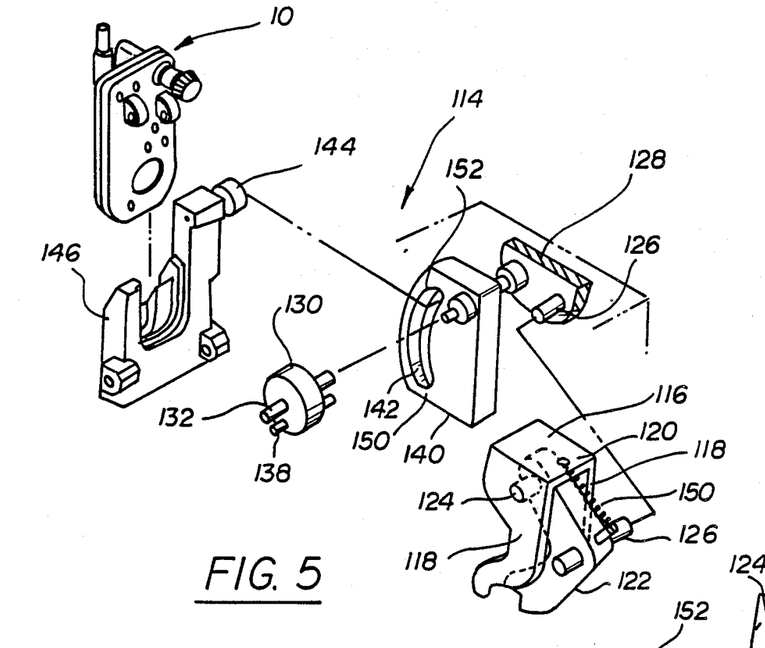
FIG. 5 is a perspective view of the cassette of the present invention along with the flow regulator shutoff assembly of a driver mechanism used to operate the cassette of the present invention.
Figure 6:
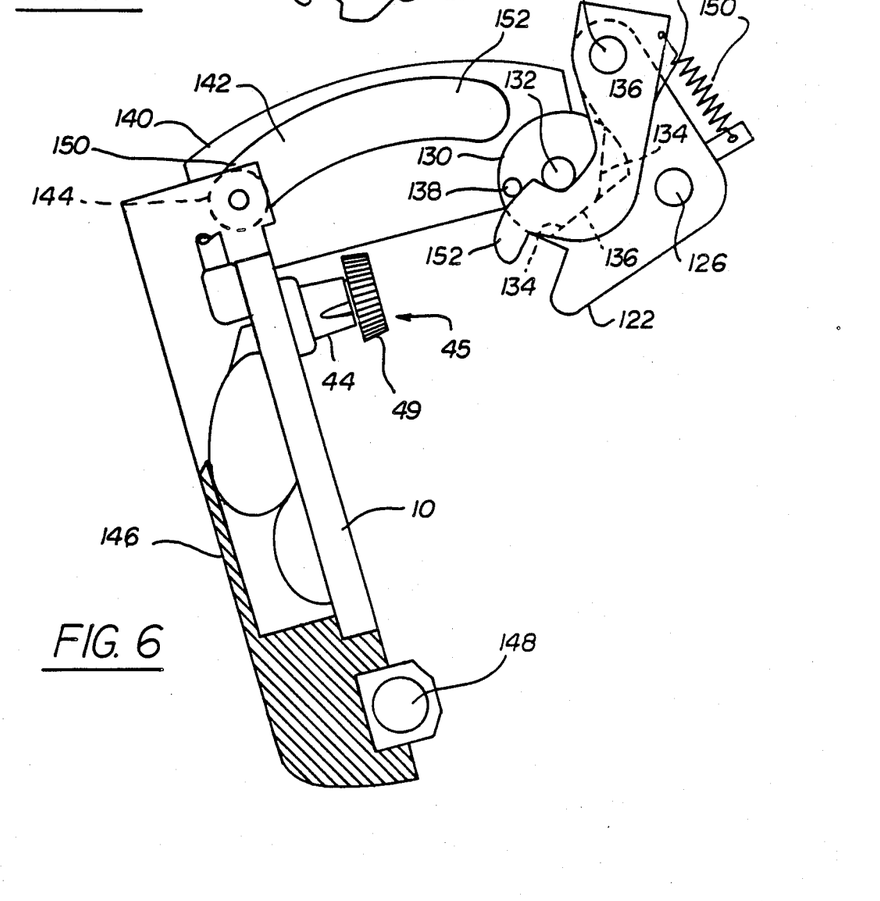
FIG. 6 is a detailed view partially in section of the cassette mounted in a door of a driver having a regulator shutoff assembly.

As can be seen in FIG. 6, when driver door 146 is open, pivot arm 140 is in a substantially horizontal position with roller 144 at the distal end 150 of slot 142. When door 146 is pivoted to the vertical, closed position shown in FIG. 5, roller 144 travels in slot 142 and forces pivot arm 140 to rotate in a counterclockwise position from the position shown in FIG. 6 to the position shown in FIG. 5 where roller 144 is in the proximal end 152 of slot of 142. As pivot arm 140 pivots from the substantially horizontal position shown in FIG. 6 to the substantially vertical position shown in FIG. 5, it rotates shaft 132 since pivot arm 140 is fixedly attached to shaft 132. As shaft 132 rotates in a counterclockwise position, it forces cam 130 to do likewise. As cam 130 rotates counterclockwise (FIG. 7), the ends of driving pin 138 engage the lower ends of arms 118, forcing gripper bracket 116 to pivot about pin 124. In addition, the counterclockwise rotation of cam 130 forces depressor member 122 to pivot about pin 126. The counterclockwise rotation of cam 130 forces cam surface 134 against cam surface 136 to urge depressor member to rotate in a clockwise direction about pin 126 until cam surface 134' engages cams surface 136' as shown in FIG. 7.

Figures 8, 9:
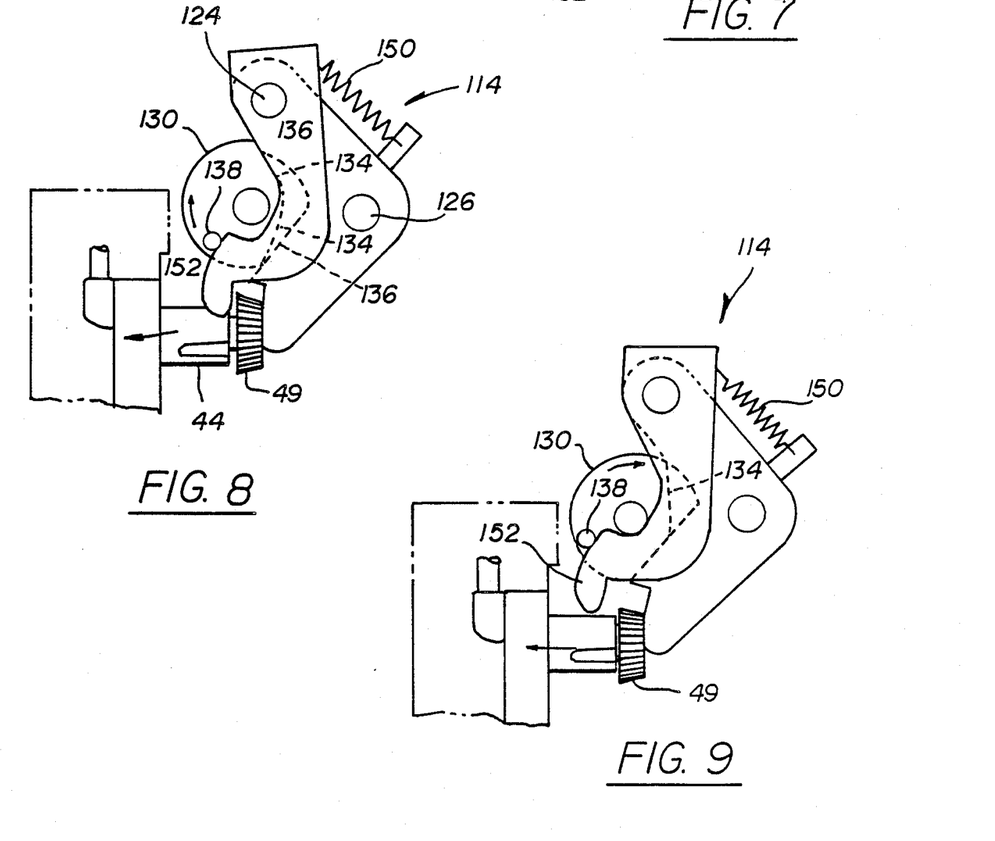

When door 146 is opened again (i.e., pivoted toward the position shown in FIG. 6), pivot arm 140 pivots from the substantially vertical position shown in FIG. 5 toward the substantially horizontal position shown in FIG. 6, forcing cam 130 to rotate clockwise (FIG. 8). As cam 130 rotates clockwise, driving pin 138 releases the lower ends of arms 118, and a spring 150 between gripper bracket 116 and depressor member 122 urges gripper bracket 116 to pivot clockwise about pin 124 to return to the position of FIG. 6.

Figure 7:
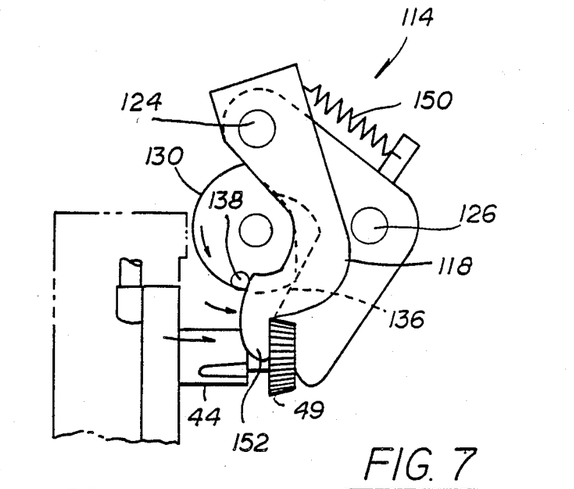
FIGS. 7-9 are detailed views of the regulator shutoff assembly of a driver employed to operate the cassette of the present invention.

As cam 130 rotates clockwise as shown in FIG. 8, cam surface 134' engages cam surface 136' to force depressor member 122 to pivot in a clockwise direction about pin 126 to return to the position of FIG. 6 from position of FIG. 7, the position of FIG. 8 being an intermediate position between the positions of FIGS. 6 and 7.

The lower ends of arm 118 include gripper fingers 152. When cassette 10 is mounted in the door and the door is pivoted toward the closed position, the knob 49 (FIGS. 6-9) of plunger 47 passes beneath the ends of fingers 152 to a position adjacent to the lower end of depressor member 122. As cam 130 drives gripper bracket 116 and depressor member 122 toward the "closed" position of FIG. 7, fingers 152 trap knob 49 between fingers 152 and the lower end of depressor member 122 and pull plunger 47 outwardly of cylindrical housing 44 to open the flow regulator 45 completely.

Conversely, when door 146 is pivoted from the closed position toward the opened, roller 144 forces pivot arm 140 to rotate cam 130 in a counterclockwise direction which allows fingers 152 to move away from the lower end of depressor member 122 to release knob 49 from flow regulator shutoff assembly 114. As knob 49 is being released, cam 130 pivots depressor member 122 such that the lower end of depressor member 122 depresses or urges plunger 47 inwardly of housing 44 (see FIGS. 8 and 9) so that flow regulator 45 is closed and prevents fluid from flowing through the cassette. When the door is fully opened (FIG. 6), the flow regulator is off, and the cassette can be removed. It is important that the flow regulator be turned off before the cassette is removed otherwise, fluid would flow through the cassette in an uncontrolled fashion under the force of gravity.

As can be seen, when cassette 10 is mounted in the cassette driver and driver door 146 is closed, flow regulator 45 is opened completely by shutoff assembly 114. However, when door 146 is opened to remove cassette 10 from the driver, shutoff assembly closes flow regulator 45 to prevent fluid from flowing through the cassette an an uncontrolled rate. After the cassette is removed, plunger 47 can be manually threaded outwardly of regulator 45 to allow fluid to be administered to the patient at a controlled rate, if desired.

Figure 14:
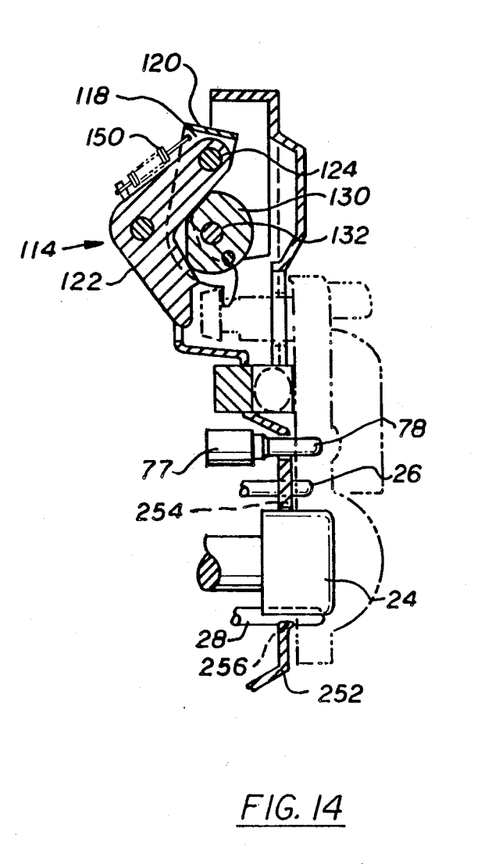
FIG. 14 is a cross section taken along the plane of line 14—14 of FIG. 13 showing a cassette of the present invention in phantom.
Figure 15:
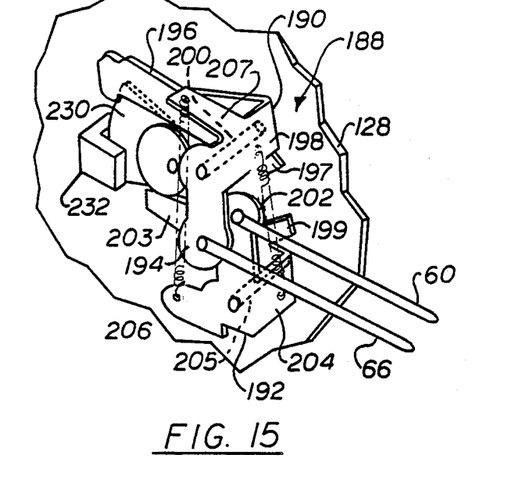
FIG. 15 is a detailed perspective view of the cassette primary and secondary inlet actuator drive assembly of the present invention.

As indicated above, flow regulator shutoff assembly 114 opens flow regulator 45 completely when cassette 10 is mounted on door 146 and door 146 is closed. To prevent fluid from flowing through the cassette at an uncontrolled rate before plunger 24 begins pumping fluid, pumping chamber inlet valve actuator 28 and/or pumping chamber outlet valve actuator 26 are positioned before pumping begins so as to block flow of fluid through the cassette, as shown in FIG. 14. Accordingly, before the cassette is placed in the cassette driver mechanism, the flow of liquid is controlled manually by flow regulator 45 at a rate set by medical personnel. This manual rate can range from zero to the maximum gravity flow rate through the cassette. When the cassette is placed in the driver mechanism, however, regulator shutoff assembly 114 opens flow regulator 45 completely, but valve actuators 26 and/or 28 stop fluids from flowing through the cassette until the cassette driver pumping sequence and rates are selected by medical personnel. Finally, when the cassette is removed from the cassette driver mechanism, flow regulator shutoff assembly 114 shuts off flow regulator 45 until flow regulator 45 can be reset manually by medical personnel at the desired rate if such reset is desired.

III. Air-In-Line Detection System

As previously indicated, the air-in-line detection system includes an air-in-line detector 34 located in the fluid path between cassette inlets 32, 64, and drip chamber 90. The air-in-line detection system also includes an air-in-line detector 36 positioned in the fluid path between pressure detection chamber 82 and flow regulator 45. Air-in line detectors 34 and 36 are substantially identical to each other.

The air-in-line detection system also includes a pair of ultrasonic detectors mounted on the cassette driver—an ultrasonic detector 154 (FIG. 1) for air-in-line detector 34, and an ultrasonic detector 156 for air-in-line detector 36. Ultrasonic detector 154 is identical to ultrasonic detector 156. Therefore, only air-in-line detector 34 and ultrasonic detector 154 will be described in any detail. Furthermore, they are described in U.S. patent application Ser. No. 045,951 filed on an even date herewith entitled Ultrasonic Detector, the disclosure of which is incorporated herein by reference.

Figure 11:
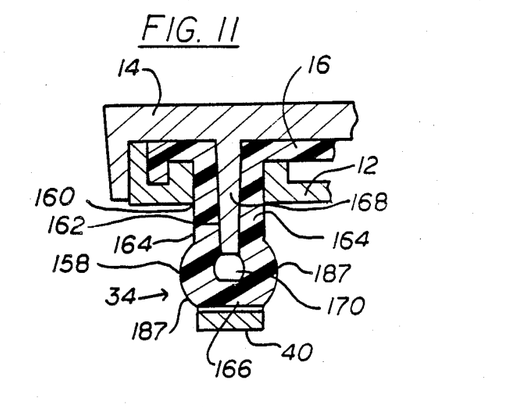
FIG. 11 is a cross section taken along the plane of line 11 of FIG. 1.

Air-in line detector means 34 includes a pocket 158 formed integrally as part of elastomeric member 16 (see FIGS. 3, 10 and 11). Pocket 158 extends through an opening 160 (FIG. 11) in face member 12 and projects outwardly beyond the surface of face member 12. Pocket 158 has a hollow recess 162 in it which is formed between two sidewalls 164 and 164' and an arcuate endwall 166. A finger 168 projects from the inner surface of back member 14 into recess 162 and fits interferingly between sidewalls 164 and 164', but does not contact endwall 166. Thus, an arcuate fluid passage 170 (see FIGS. 3 and 11) is formed between the inside surfaces of endwall 166 and the perimeter of finger 168 which forms part of the fluid path through the cassette. Fluid passage 170 allows the fluid flowing through the cassette fluid path in the cassette to loop outwardly from the surface of face member 12 so that any air in the fluid path can be detected by ultrasonic detector 154 (or 156) outside of the cassette. Guard member 40 (FIGS. 3 and 11) covers and protects the outside of endwall 166 to prevent endwall 166 from being crushed or damaged. Ultrasonic detectors 154 and 156 are mounted on a cassette driver, a nondisposable item, whereas the cassette is inexpensive and disposable after each use.

Figure 12:
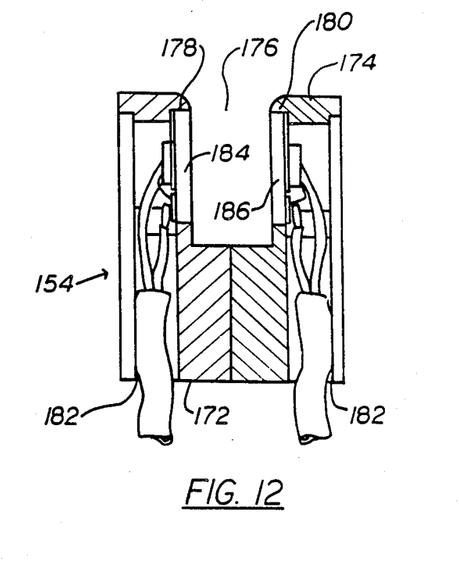
FIG. 12 is a sectional view of an acoustic coupling employed in the air-in-line detection system of the present invention.
Figure 13:
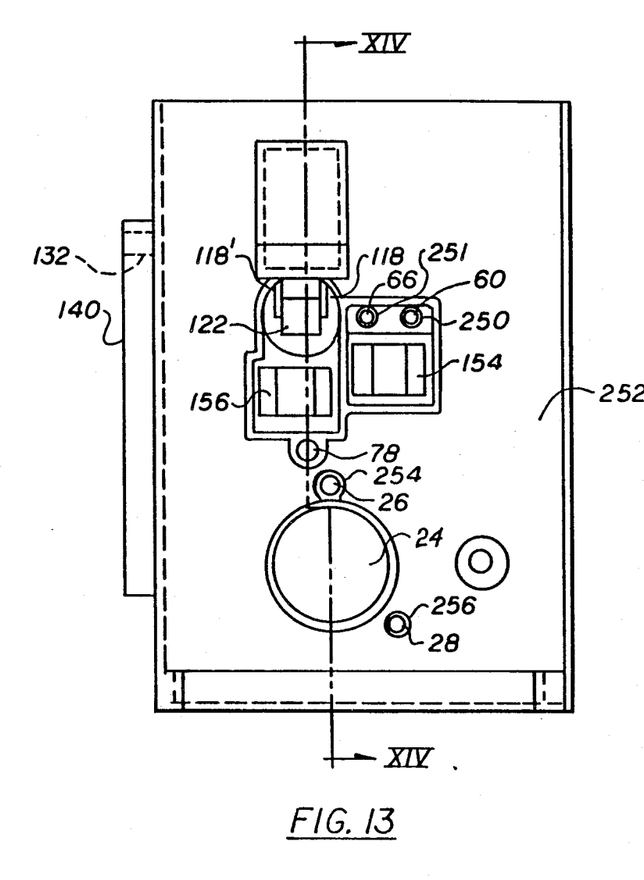
FIG. 13 is a front elevation of a portion of the front panel on the driver employed to drive the cassette of the present invention shown with the cassette door removed.

Ultrasonic detector 154 (see FIGS. 1, 10 and 12) includes two mirror housing portions 172 and 174. Housing member 172 is generally L-shaped and is joined to the mirror imaged L-shaped housing 174 at the bottom of the L's so as to form a U-shaped housing assembly with a recess 176 between the arms of the U adapted to receive air-in-line detector 34. On one side of recess 176, housing portion 172 has an opening 178, while on the other side of recess 176, housing portion 174 has an opening 180. Housing members 172 and 174 are hollow, each containing a passage 182 for the necessary electrical contacts. Positioned in opening 178 is an ultrasonic generator 184, facing an ultrasonic receiver 186 positioned in opening 180. Ultrasonic generator 184 is positioned directly across recess 176 from ultrasonic receiver 186.

Figure 25:
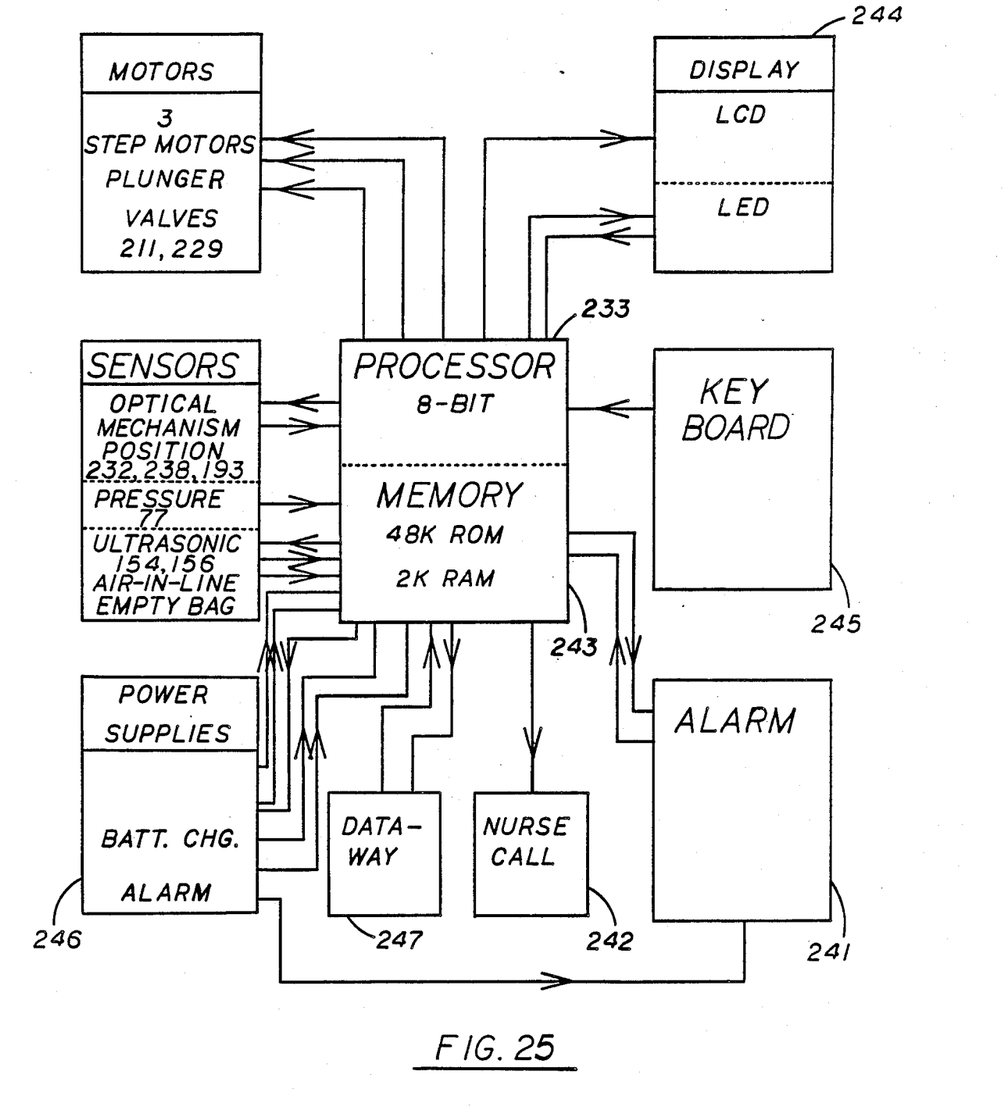
FIG. 25 is a schematic of the operating system of the cassette driver of the present invention

Elastomeric pocket 158 has two resilient lobes 187, 187' (FIGS. 1 and 11) which extend outwardly from sidewalls 164, 164' in opposite directions. The width of pocket 158 between lobes 187, 187' is somewhat less than the width of recess 176 between ultrasonic generator 184 and ultrasonic receiver 186 so that lobes 187 and 187' are compressed inwardly toward each other when air-in-line detection means 34 is inserted into ultrasonic detector 154 as shown in FIG. 10. This insures that there will be good acoustic contact between ultrasonic generator 184 and pocket 158 and between ultrasonic receiver 186 and pocket 158. Thus, an ultrasonic signal can be transmitted across fluid passage 170 when air-in-line detecting means 34 is inserted into recess 176. The transmission of ultrasonic sound between ultrasonic generator 184 and ultrasonic receiver 186 is greatly enhanced when a liquid is present in passage 170. But when air is present in passage 170, the transmission of ultrasonic sound through fluid passage 170 is attenuated. This difference in ultrasonic sound transmission is detected by ultrasonic receiver 186. When air is present, the electrical signal generated by ultrasonic receiver 186 decreases. Ultrasonic detector 154 (and 156) is coupled to a microprocessor 233 (FIG. 25) which receives an amplified signal generated by ultrasonic receiver 186 and subsequently amplified. Microprocessor 233 is preferably a 63B03R Hitachi microprocessor. When the signal received by processor 233 from receiver 186 decreases, an alarm 241 (FIG. 25) is sounded by processor 233 to stop the pumping of fluid through the cassette if the cassette is in the fluid delivery cycle. Thus, when a container of medical fluid is connected either to cassette inlets 32 or 64 is emptied, any air drawn into the cassette from the empty containers will be drawn through air-in-line detector 34, and the presence of that air will be detected by ultrasonic detector 154. Alarm 241 and/or nurse call 242 is then sounded, and the cassette driver is stopped to prevent further pumping. If ultrasonic detector 154 malfunctions and does not detect the presence of air, the air pumped will be detected by ultrasonic detector 156. Likewise, if there is an air leak in the system between the fluid container and the outlet of the cassette before the fluid container is emptied, any air drawn into the system will be detected by one or the other ultrasonic detectors 154 or 156 through air-in-line detectors 34 and 36. Other functions of the air-in-line detection system will be explained in the "Operation" section below.

Further details of the air-in-line detection system of the present invention can be found in the aforementioned patent application Ser. No. 045,951 filed on the same date herewith entitled Ultrasonic detector.

IV. Plunger 24

Plunger 24 and its operation is described in detail in U.S. patent application Ser. No. 811,262 filed Dec. 20, 1985 entitled "Fluid Infusion Pump Driver", the disclosure of which is incorporated herein by reference.

V. Valve Actuator Assemblies

As indicated previously, valve actuators 60 and 66 operate the secondary and primary cassette inlet valve, and valve actuators 26 and 28 operate the pumping chamber inlet and outlet valves. Similar mechanisms are employed to operate each of these pairs of valve actuators. The valve actuator assembly 188 drives valve actuators 60 and 66 (FIGS. 15-19). Valve actuator assembly 188 includes a first bracket 190 which drives valve actuator 66. First bracket 190 includes two arms 194 and 196 which are spaced from and perpendicular to each other, and joined to each other by a bight portion 198. First bracket 190 is pivotally mounted on the chassis 128 of the driver by a pivot pin 200 which is located at the proximal ends of arms 194 and 196 joined by portion 198 so that arms 194 and 196 pivot about a common pivot point when operated as described below. Valve actuator 66 is pivotally secured to the distal, free end of arm 194. The distal, free end of arm 196 is driven by a cam 201 as described below Valve actuator assembly 188 also includes a second bracket 192 with two spaced, perpendicular arms 202 and 203, which are joined to each other by a bight portion 204. Second bracket 192 is pivotally mounted on chassis 128 by a pivot pin 205 which is located at the ends of arms 202 and 203 joined by bight portion 204. The free end of arm 202 is pivotally connected to valve actuator 60. The free end of arm 203 engages cam 201 described below.

A primary spring 206 biases brackets 190 and 192 around pins 200 and 205 such that arms 196 and 203 are urged toward cam 201. One end of spring 206 is connected to a tab 207 which extends from bight portion 198. The other end of primary spring 206 is connected to a tab 208 which extends from the proximal end of arm 202. Tabs 207 and 208 generally extend toward cam 201 so that spring 206 will bias arms 196 and 203 toward cam 201.

A secondary spring 209 is attached to and between bight portions 198 and 204 to urge arms 196 and 203 away from cam 201 in the event that primary spring 206 breaks. However, secondary spring 209 is weaker than primary spring 206 such that when the two springs are operable, arms 196 and 203 will be urged toward cam 201. If primary spring 206 breaks, secondary spring 209 will urge brackets 190 and 192 to pivot around pins 200 and 205 such that arms 196 and 203 pivot away from cam 201. The distal end of arm 196 includes a flag portion 191 (FIGS. 17 and 18) which passes through an optical switch 193 in the event of primary spring breakage. When optical switch 193 is tripped, a signal is relayed to processor 233 which stops the driver immediately and sounds alarm 241 and/or nurse call 242. A stop 195 is positioned adjacent cam 201, and brackets 190 and 192 have stop tabs 197 and 199 which project from the proximal ends of arms 196 and 203. If primary spring 206 breaks, brackets 190 and 192 will pivot around pins 200 and 205 until stop tabs 197 and 199 contact stop 195 before which point flag portion 191 would have passed through switch 193.

Figure 17:
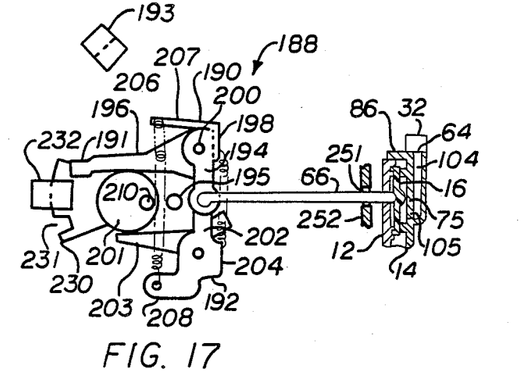
FIGS. 17-19 are detailed side elevational views of the cassette inlet and outlet actuator drive assembly of the present invention.
Figure 18:
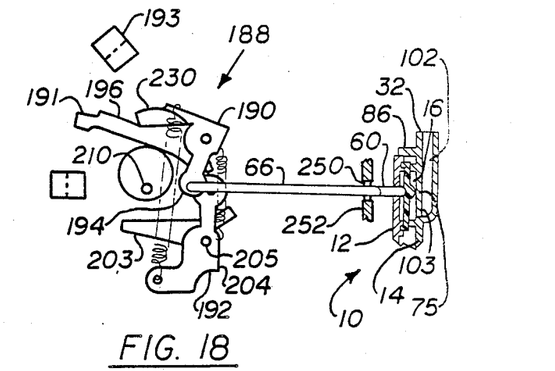
Figure 19:
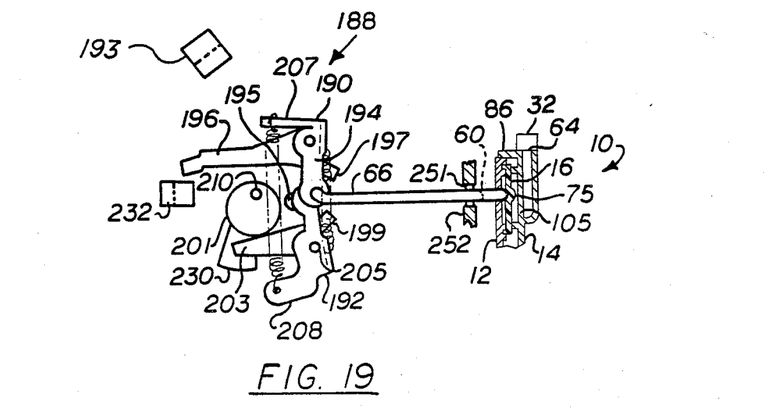

As shown in FIG. 17-19, actuators 60 and 66 are elongated rods. As indicated previously, the proximal ends of actuators 60 and 66 are pivotally connected to arms 194 and 202 of brackets 190 and 192, respectively. The distal ends of actuators 60 and 66 are supported in openings 250 and 251 (FIGS. 13 and 17-19) in the front panel 252 of the driver.

Figure 16:
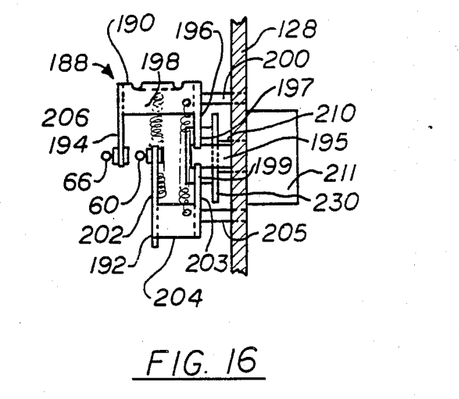
FIG. 16 is a detailed front elevational view of the cassette primary and secondary inlet actuator drive assembly of the present invention.

Cam 201 is circular in shape and is eccentrically mounted on a motor shaft 210. Shaft 210 is operated by a stepper motor 211 (FIG. 16). When cassette 10 is placed in driver door 146 and the driver door is closed to its vertical position, cam 201 is moved to the position where both valve actuators 60 and 66 are fully extended (FIG. 17) toward cassette 10 so as to close the primary and secondary cassette inlet valves. Specifically, valve actuators 60 and 66 urge elastomeric member 16 across the fluid passages leading from inlets 103 and 105 into the cassette. When a liquid is to be pumped through primary cassette inlet 64, primary inlet actuator 66 is retracted by the clockwise rotation of cam 201 by motor 211 from the position shown in FIG. 17 to the position shown in FIG. 18. Cam 201 engages arm 196 of bracket 190 and urges bracket 190 to pivot clockwise about pivot pin 200 against the bias of spring 206. As bracket 190 pivots about pivot pin 200, arm 194 retracts actuator 66, thereby allowing liquid to flow through primary cassette inlet 64 through opening 105.

When cam 201 is in the position as shown in FIG. 1 with the primary cassette inlet valve open, the secondary inlet actuator 60 remains in the extended position, urging elastomeric member 16 across the fluid passage from inlet 103 (FIG. 18) into the cassette. Secondary inlet actuator 60 is held in the extended position by the bias of primary spring 206. When cam 201 is in the position shown in FIG. 18, arm 203 does not contact it. Primary spring imparts a clockwise bias to second bracket 192 which urges actuator 60 into the closed position shown in FIG. 18. Since cassette 10 is in a fixed position in the driver door 146 when cassette 10 is mounted in the driver, cassette 10 acts as a stop to prevent arm 203 from contacting cam 201 when primary inlet actuator 66 is retracted as shown in FIG. 18.

When fluid is to be pumped through secondary cassette inlet 32, motor 211 is reversed and turns cam 201 counterclockwise from the position shown in FIG. 18 to the position shown in FIG. 19 where cam 201 engages arm 203 of second bracket 192 and pivots bracket 192 counterclockwise about pivot pin 205. When arm 202 of bracket 192 pivots counterclockwise, valve actuator 60 is retracted allowing fluid to flow through opening 103 into the cassette. When the secondary cassette inlet is open, the primary cassette inlet remains closed because primary cassette inlet actuator 66 remains in the extended position under the bias of primary spring 206. When cam 201 is in the position as shown in FIG. 19, arm 196 of first bracket 190 no longer contacts cam 201 because cassette 10 operates as a stop against clockwise rotation of bracket 190 under the bias of spring 206 when cam 201 is in that position. This keeps the secondary cassette inlet closed while the primary inlet is open.

It can be seen, therefore, that cassette inlet valve actuator assembly 188 allows the following possible cassette inlet valve positions: (1) both the primary and secondary cassette inlet valves closed; (2) the primary inlet valve open and the secondary inlet valve closed; and (3) the secondary cassette inlet valve open and the primary cassette inlet valve closed. In normal operation, valve actuator assembly 188 does not permit both the primary and secondary cassette inlet valves to be open simultaneously.

Figure 20:
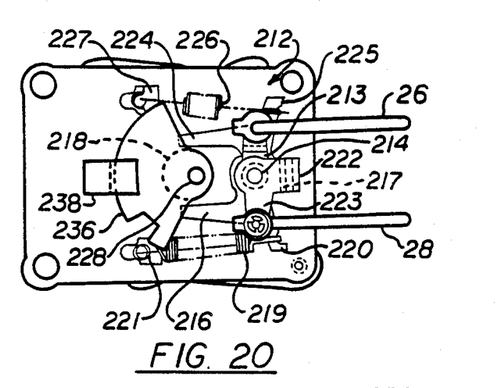
FIG. 20 is a detailed side elevational view of the pumping chamber inlet and outlet actuator drive assembly of the present invention.
Figure 21:
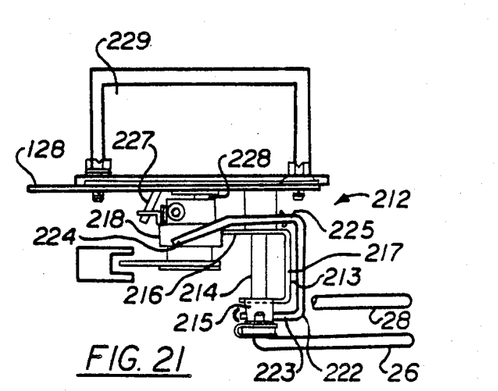
FIG. 21 is a detailed plan view of the pumping chamber inlet and outlet actuator drive assembly of the present invention.

A second valve actuator assembly 212 is used to operate pumping chamber outlet and inlet valve actuators 26 and 28 (FIGS. 20-21). Pumping chamber outlet valve actuator 26 is operated by a first bracket 213 which is pivotally mounted on a pivot pin 214 on chassis 128. First bracket 213 has two spaced, perpendicular arms 215 and 216 fixedly secured and integrally formed with a bight portion 217. The proximal end of arm 215 is pivotally secured to pivot pin 214, and the distal end of arm 215 is pivotally secured to actuator 26. The proximal end of arm 216 is pivotally mounted to pivot pin 214, and the distal end of arm 216 is urged toward a cam 218 described below by a spring 219. One end of spring 219 is attached to a tab 220 which extends from the proximal end of arm 216. The other end of spring 219 is attached to a tab 221 raised from chassis 128. Spring 219, therefore, biases first bracket 213 such that arm 216 will be urged toward a cam 218.

Valve actuator assembly 212 also includes a second bracket 222 pivotally mounted about pivot pin 214. Second bracket 222 includes a first arm 223, the proximal end of which is pivotally secured to pin 214, and the distal end of which is pivotally secured to the proximal end of valve actuator 28. Second bracket 222 also includes a second arm 224, the proximal end of which is pivotally secured about pin 214, the distal end of which is free to be engaged by cam 218. Arms 223 and 224 are perpendicular to each other and fixedly joined to each other by a bight portion 225. Second bracket 222 further includes a tab 225 which extends from the proximal end of second arm 224. The free end of tab 225 is attached to one end of a spring 226 which biases arm 224 toward cam 218. The other end of spring 226 is attached to a tab 227 which is raised from chassis 128.

Cam 218 is eccentrically mounted on a motor shaft 228 operated by a stepper motor 229. As cam 218 is driven by motor 229 in counterclockwise from the position shown in FIG. 20, cam 218 engages arm 216, forces first bracket 213 to pivot counterclockwise about pin 214, and causes valve actuator 26 to retract against the bias of spring 219. When valve actuator 26 is retracted, the pumping chamber outlet valve is opened. When cam 218 is driven counterclockwise against arm 216, arm 224 of bracket 222 remains stationary, and spring 226 will force valve actuator 28 to remain extended against the pumping chamber inlet valve, keeping pumping chamber inlet valve closed. As cam 218 is driven by motor 229 in a clockwise from the position shown in FIG. 20, it engages arm 224, pivots bracket 222, and forces valve actuator 28 to retract against the bias of spring 226, opening the pumping chamber inlet valve. When cam 218 is driven counterclockwise against arm 224, arm 216 of bracket 213 remains stationary, and spring 219 will force valve actuator 26 to remain extended against the pumping chamber outlet valve, keeping the pumping chamber outlet valve closed. It can be seen that valve actuator assembly 212 permits both the pumping chamber inlet and outlet valves to be closed, or allows only one of them to be opened at a time. More importantly, valve actuator assembly 212 prevents both the pumping chamber inlet and outlet valves from being opened simultaneously so that fluid cannot flow through the cassette at an uncontrolled rate under the force of gravity during the pumping cycle.

The proximal ends of actuators 26 and 28 are pivotally connected to brackets 215 and 223, as indicated above. The distal ends of actuators 26 and 28 are supported in openings 254 and 256 (FIGS. 14 and 15) in front panel 252. Since valve actuator assemblies 188 and 212 are driven by separate motors 211 and 229, and since plunger 24 is driven by a motor separate from stepper motors 211 and 229, the three motors must be operated in a synchronized fashion, and the positions of each during the operations of the cassette driver must be monitored.

Figure 23:
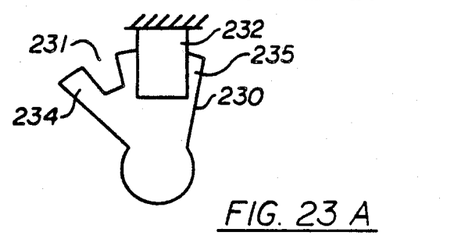

To monitor the position of cam 201 of valve actuator assembly 188 (and hence monitor the position of valve actuators 60 and 66), a flag 230 is fixedly mounted on cam 210. Flag 230 is thin, pie-shaped strip of metal with a small notch 231 on its radial edge. As cam 201 moves counterclockwise from the position shown in FIG. 18 to the position shown in FIG. 19, motor 211 takes a set number of steps, preferably 24 steps. Notch 231 is not centered on the radial edge of flag 230, but is offset to one side. Valve actuator assembly 188 further includes an optical switch 232 through which the radial edge of flag 230 passes as cam 201 moves from position shown in FIG. 18 to the position shown in FIG. 19 and back again during its normal operation. Optical switch 232 passes a beam of light across the space through which flag 230 passes. Flag 230 breaks the beam of light as it is passing through, except for notch 231 which allows light to pass when notch 231 passes through switch 232. Optical switch 232 is coupled to microprocessor 233 (FIG. 25) to relay to microprocessor 233 whether light is being transmitted or whether it is being blocked by flag 230. Microprocessor 233 also controls stepper motor 211 such that as the stepper motor 211 moves stepwise clockwise or counterclockwise, the microprocessor can determine whether cam 201 is out of position. For instance, as flag 230 passes through switch 232 as it moves from the position shown in FIG. 18 to the position shown in FIG. 19, there will be a fairly large number of steps in which light is transmitted across switch 232 before flag 230 breaks the optical beam and prevents light from being transmitted. As flag 230 continues its movement towards position shown in FIG. 19, there will be a small number of steps during which the radial edge portion 234 (FIG. 23A) counterclockwise of notch 231 prevents the passage of light. Then, notch 231 will pass through optical switch 232, allowing light to pass for a small number of steps, whereupon the larger radial edge portion 235 passes through switch 232 for a fairly large number of steps of motor 211. This is followed by a fairly large number of steps where light passes across switch 232 after portion 235 passes through switch 232.

It can be seen that as cam 201 moves from position shown in FIG. 18 to the position shown in FIG. 19, there will be a pattern of a short number of steps when portion 234 passes through switch 232 followed by a short number of steps in which notch 231 passes through switch 232 and a longer period of time in which portion 235 passes through notch 232. This repeated dark/light/dark pattern is correlated by microprocessor 233 to the position where cam 201 should be during its cycle. If motor 211 is not "in synch" with the preprogrammed dark/light/dark values in microprocessor 233, microprocesser 233 can advance or retard motor 211 the appropriate number of steps to synchronize the positions of valve actuators 60 and 66 with the positions where they should be during driver operation.

Similarly, in valve actuator assembly 212, cam 218 has a flag 236 attached to it. Flag 236 is generally pie shaped, having a radial edge with a notch 237 in it. An optical switch is positioned so that flag 236 passes through it as flag 236 moves from the position shown in FIG. 22(B) where valve actuator 26 is retracted to the position shown in FIG. 22(C) where valve actuator 28 is retracted. Notch 237 is likewise offset to provide a small radial edge portion 239 and a large radial edge portion on either side of notch 237. Thus, when flag 236 moves from the position shown in FIG. 22(C) to the position shown in FIG. 22(C), switch 238 will detect a short period of darkness as radial edge portion 239 passes, a short period of light when notch 237 passes, and a long period of darkness as portion 240 passes through switch 238. Microprocessor 233 is coupled to optical switch 238 such that the periods of light and darkness can be correlated stepwise to the number of steps taken by stepper motor 229 between the positions of FIGS. 22(C) and 22(B). Therefore, as flag 236 moves back and forth between these two positions opening and closing the pumping chamber inlet and outlet valves, microprocessor 233 can compare the actual position of cam 218 (and hence the positions of valve actuators 26 and 28) with the desired, preprogrammed position to either advance or retard stepper motor 229 appropriately Not only are the positions of cams 201 and 218 monitored during the pumping cycle, but the positions of the cams are checked before pumping begins. After the cassette is placed in door 146 and the door is closed, motor 211, for instance, will drive cam 201 back and forth between the position shown in FIGS. 18 and 19 while optical switch 232 checks the actual position of flag 230, and microprocessor 233 will stop stepper motor 211 once it is determined that cam 201 is in the proper position to begin the pumping sequence. In the case where only a single fluid is to be pumped, for instance, that position will b when valve actuator 56 is retracted and valve actuator 60 is extended (FIG. 18).

Figure 22:
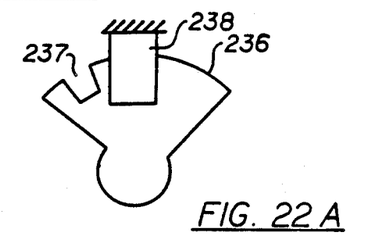

Similarly, during this pre-pumping check, motor 229 will move flag 236 and cam 218 back and forth between the positions of FIGS. 22(B) and (C) to position the pumping chamber inlet and outlet valve actuators 26 and 28 in their appropriate positions to begin the pumping cycle, namely, with both valve actuators 26 and 28 fully extended, (i.e., the positions shown in FIGS. 20, and 22(A). Thus, the pumping chamber inlet and outlet valves can be checked according to the procedure described below. Once microprocessor 233 verifies that flag 236 is in the proper position, the valve checking sequences and pumping sequences described below can commence.

Plunger 24 is also operated with a stepper motor (not shown). An optical flag is also attached to the plunger stepper motor shaft so that an optical switch (not shown) and microprocessor 233 monitor and position plunger 24 before and during the pumping cycle to synchronize plunger 24 with the operation of actuators 26, 28, 60, and 66.

VI. Operation

When pumping only one liquid at a time, the liquid container with the liquid to be pumped is connected to primary cassette inlet 64, and the secondary cassette inlet 32 is closed with a luer type locking cap (not shown). The cassette is primed with fluid by opening regulator 45 and initially inverting the cassette from the position shown in FIG. 2 to purge the fluid path between the cassette inlets and the pumping chamber of air (except, of course, for the trapped volume 100). The pumping chamber and the fluid path beyond it are purged of air by returning the cassette to the upright position of FIG. 2. Regulator 45 is then either closed or set manually to a desired flow rate until the cassette is mounted in the cassette driver. Once the cassette is mounted in the driver, the flow regulator shutoff assembly 114 automatically opens regulator 47 and the cassette valves are tested as described below.

Figure 24:
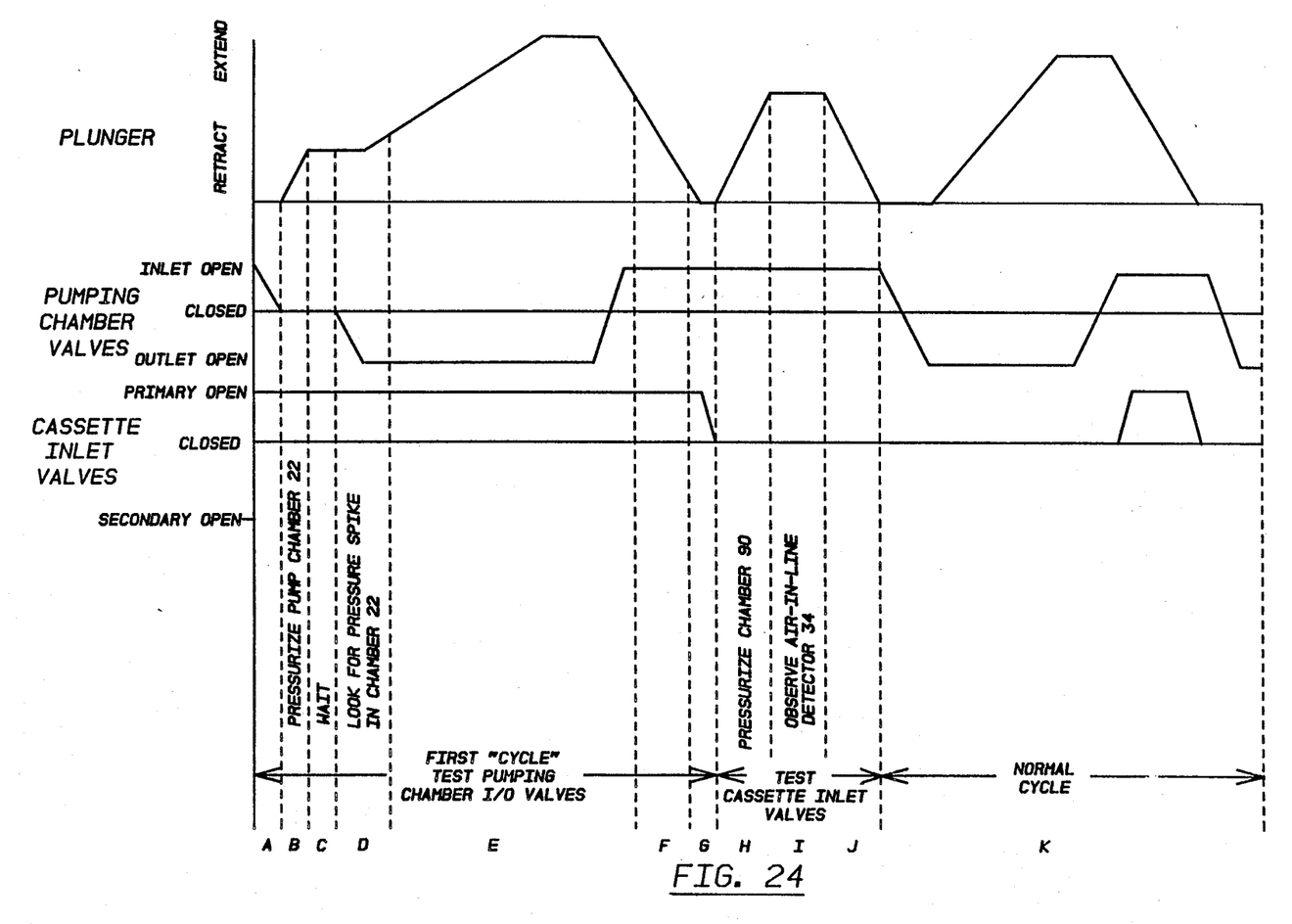
FIG. 24 is a graphical representation of the pumping sequence of the cassette driver of the present invention.

Once the cassette inlet valve actuators 60 and 66, pumping chamber inlet and outlet valve actuators 26 and 28, and plunger 24 are properly synchronized as described above, air-in-line detector 34 and pressure detection chamber 82 are used to test whether valve actuators 26, 28, 60, and 66 are cooperating with the disposable cassette 10 to provide adequate valving of fluid in the cassette. The sequence for such testing is illustrated in FIG. 24. To test the inlet and outlet valves of pumping chamber 22, inlet valve actuator 28 and outlet valve actuator 26 are extended into openings 68 and 72, respectively to block flow of fluid into and out of pumping chamber 22 Step A FIG. 24). With valve actuators 26 and 28 in the extended positions, plunger 24 is urged against elastomeric member 16 across plunger opening 18 to pressurize pumping chamber 22 (Step B). Plunger 24 is held in this position for the "WAIT" period (Step C), pressurizing chamber 22 for a short period of time, whereupon outlet valve actuator 26 is retracted to allow pressurized liquid to escape pumping chamber 22, while inlet valve actuator 28 is held in its "extended" position (Step D). When outlet valve actuator 26 is released (Step D), the pressurized liquid within chamber 22 surges into pressure detection chamber 82, producing a pressure pulse or spike in chamber 82. When the pumping chamber inlet and outlet valves are functioning properly, the magnitude of this pulse will be constant from cassette-to-cassette. However, when a cassette with poorly functioning pumping chamber inlet and/or outlet valves is encountered, the pressure pulse produced within chamber 82 during this valve test procedure will be noticeably lower because a certain amount of pressurized liquid from chamber 22 will have leaked past either the pumping chamber inlet or outlet valves during the "WAIT" period. If the pressure pulse produced by this test procedure in pressure detection chamber 82 is lower than expected, it is assumed that the pumping chamber inlet and/or outlet valves are functioning improperly so that the cassette is rejected.

The magnitude of the spike is detected by pressure sensor 77 which is coupled to microprocessor 233. The details of the operation of pressure sensor 77 are described in U.S patent application Ser. No. 045,949 filed May 1, 1987 entitled PRESSURE SENSOR ASSEMBLY FOR DISPOSABLE PUMP CASSETTE filed on an even date herewith by Fellingham et al, which is incorporated herein by reference. Microprocessor 233 compares the value of the signal generated by sensor 77 to a stored value. If the stored value is significantly greater, microprocessor 233 will sound an alarm 241 and a nurse call 242 and the pump driver will not function unless a new cassette is used.

The pump chamber inlet and outlet valve test procedure described above is first done automatically by the cassette driver immediately after the driver is started. Thereafter, the same test procedure can be done periodically during fluid delivery to insure the continuing integrity of the pumping chamber inlet and outlet valves during fluid delivery.

The test procedure is performed periodically in the fashion illustrated in FIG. 24, steps A-E. The pumping chamber inlet valve is closed (step A) while the pumping chamber outlet valve is closed. Chamber 22 is pressurized by extending plunger 24 a short distance into chamber 22 (step B). The plunger is held for the "WAIT" period (step C). The pumping chamber outlet valve is opened and the pressure spike detected in chamber 22 (step D). If the pressure spike is of sufficient magnitude, plunger 24 extends further into chamber 22, (step E) to displace the rest of the fluid in chamber 22 and pump it into the patient. The pumping chamber outlet valve is closed (last part of step E), and the inlet valve is opened (step F) while the plunger is retracted to fill the pumping chamber with liquid.

Once it is initially established that the pumping chamber inlet and outlet valves are working properly, air-in-line detector 34 can be used to establish whether the cassette inlet valves associated with primary cassette inlet 64 and secondary cassette inlet 32 are working properly. To test the cassette inlet valves, the pumping chamber outlet valve is closed and the pumping chamber inlet valve is open (end of step E). At the same time, the two inlet valves 64 and 32 are closed (step G), and plunger 24 pressurizes pump chamber 22 (step H). The system is then held pressurized for a short period of time (step I). If either of the two cassette inlet valves leak, liquid will flow out of the primary cassette inlet 64 or secondary cassette inlet 32. This reverse displacement of fluid will be accompanied by the movement of trapped air 100 in drip chamber 90 upwardly into air-in-line detector 34 as shown in FIG. 3. Ultrasonic detector 154 will detect this presence of air, and relay this to microprocessor 233 which sounds alarm 241 and nurse call 242. Thus, the cassette will be rejected. If the primary and secondary cassette inlet valve are good, plunger 24 is retracted (step J) for the "normal cycle" (step K) of fluid delivery described below.

In the "normal cycle" pumping sequence with only one liquid being administered. The pumping chamber inlet valve is closed and the pumping chamber outlet is opened whereupon plunger 24 is urged through opening 18 against elastomeric member 16 to displace the fluid from pumping chamber 22 out cassette outlet 30 to the patient. The amount of fluid during the fluid delivery stroke is controlled precisely by operating plunger 24 with a conventional stepping motor. By operating plunger 24 with a stepper motor, the displacement of plunger 24 against elastomeric member 16 can be controlled precisely for each delivery stroke by advancing the stepper motor the same number of steps for each delivery stroke such that a constant volume of fluid is displaced from pumping chamber 22 for each stroke.

To refill pumping chamber 22 for the next delivery stroke, the pumping chamber outlet valve is closed, the pumping chamber inlet and the primary cassette inlet valves are opened, and then plunger 24 is retracted the same number of steps it was advanced during the previous fluid delivery stroke. Since both the pumping chamber inlet valve and the primary cassette inlet valve are opened, fluid will be drawn from the fluid container connected to the primary cassette inlet as plunger 24 is retracted stepwise. Once plunger 24 is retracted to its starting or "home" position, the pumping chamber inlet and the primary cassette inlet valves are closed and the pumping chamber outlet valve is opened for the next stepwise fluid delivery stroke of plunger 24. The fluid delivery stroke is then repeated followed by the pumping chamber refill retraction stroke by plunger 24 with the pumping chamber inlet and outlet valves appropriately valving the flow of fluid on delivery and refill. As can be seen, the pumping of fluid when a single fluid is being pumped is fairly simple and straightforward.

However, multiple fluid delivery is also possible. When two liquid are to be pumped, the container containing the primary liquid is connected to the primary cassette inlet 64. The secondary liquid container is connected to the secondary cassette inlet 32 by removing the luer lock cap on inlet 32 and connecting the secondary fluid container to inlet 32 with a luer connector. The valving of the pumping chamber inlet and outlet valves during fluid delivery and pumping chamber refill strokes are the same during a two-fluid delivery as with the single fluid delivery procedure described above. However, the cassette inlet valving is different. During single fluid delivery, of course, the secondary cassette inlet valve is always closed and only the primary inlet valve is open during the refill of the pumping chamber. However, when pumping two fluids, the primary and secondary cassette inlet valves are each opened and closed for selected periods of time during the pumping chamber refill stroke. For instance, if the two fluids are to be mixed in a fifty-fifty proportion, the primary cassette inlet valve is opened during the first half of the total number of strokes comprising the pumping chamber refill stroke of plunger 24. During the first half of the retraction stroke of plunger 24, the secondary cassette inlet valve is closed. However, during the second half of the retraction/refill stroke of plunger 24, the secondary cassette inlet valve is opened while the primary cassette inlet valve is closed. Since plunger 24 is controlled stepwise, it is possible to ascertain exactly when to switch the two cassette inlet valves from open to closed and vice versa to achieve the desired proportioning of the two fluids.

Often, however, the primary fluid is a diluent such as saline solution whereas the secondary fluid is a concentrated drug. In such situations, a fifty-fifty mixture may be undesirable, so the secondary cassette inlet valve may be opened only 10 to 20 percent of the steps during the pumping chamber refill stroke of plunger 25 while the primary cassette inlet valve is opened 80 to 90 percent of the steps comprising the refill stroke of plunger 24.

It can be seen, therefore, that virtually any desired concentration of secondary fluid in primary fluid can be delivered to the patient using the cassette and driver of the present invention simply by operating inlet actuator 60 and 66 in sequence and in tandem with plunger 24 during the pumping chamber refill stroke as described above. Because cassette inlet actuators 60 and 66 cannot be simultaneously retracted as described above (i.e., one is always extended closing its cassette inlet valve), one cannot get gravity flow between the primary and secondary fluid containers through the cassette.

As indicated previously, pressure sensor 77 and pressure detection chamber 82 are employed to detect whether the pumping chamber inlet and outlet valves are functioning properly. However, once the pumping chamber inlet and outlet valves are checked for proper functioning, pressure sensor 77 and pressure detection chamber 82 can also be used to monitor the patient's blood pressure. During a pumping chamber filling stroke of plunger 24 (e.g. step F in FIG. 24), the pumping chamber outlet valve is closed such that the pressure of the fluid in the fluid path from the pumping chamber outlet valve to the patient is at the patient's blood pressure. Thus, real time measurements of the patient's blood pressure can be taken through the cassette. The patient's blood pressure is stored in memory 243. During the operation of cassette 10, microprocessor will compare the patient's blood pressure to previously recorded values of the same patient's pressure. If the patient's blood pressure drops or increases dramatically over time, microprocessor 243 will sound alarm 241 and/or nurse call 242 to alert medical personnel.

Pressure sensor 77 is also used to detect occlusions in the line leading from the cassette outlet to the patient. When plunger 24 is extended during the fluid delivery stroke, the pressure in pressure chamber 82 is monitored by sensor 77 and microprocessor 233. If the pressure is excessive, it indicates the patient line has been wholly or partially occluded. Microprocessor sounds alarm 241 and nurse call 242.

Air-in line detectors 154 and 156 are also interfaced with microprocessor 233 (FIG. 25) so that microprocessor 233 will stop the driver and sound alarm 241 and nurse call 242 if air is detected in the cassette or if detector 154 detects a bad inlet valve.

A LDC/LED display 244 (FIG. 25) is also interfaced with microprocessor 244 so that input or output values of delivery rates, delivery volumes, patient blood pressure and the like can be displayed to an operator. Likewise, message codes can be displayed to tell the operator why an alarm has been sounded.

A keyboard 245 is provided to input values of delivery rates, delivery volumes, patient blood pressure, concentration and the like. Microprocessor 233 can be programmed to deliver a given volume of primary or secondary fluid over a desired period of time, for instance. It is also programmed to set the concentration of secondary liquid in primary solution when two liquids are simultaneously delivered.

An AC/DC power supply 246 is provided and includes a battery charger to continuously monitor and charge batteries provided in the driver for operation without AC current. In the event of power failure, alarm 241 is sounded.

Finally, a dataway 247 is provided to allow a printer or other display to be connected to the driver to get data printouts of patient blood pressure over time, and fluid delivery times, volumes and rates.

While one embodiment has been disclosed and described, other embodiments will become apparent to those of ordinary skill in the art. Such embodiments are to be construed within the ambit of the claims which follow, unless by their terms, the claims expressly state otherwise.

What is claimed is:

1. A mechanism for actuating a plunger-type slideable valve on a valving device, comprising
    a moveable support associated with said mechanism for holding said valving device;

a moveable gripping means on said mechanism for gripping said valve; and a linking means between said moveable support and said gripping means to transmit the movement of said support to said gripping means whereby a valving device can be placed in said moveable support, said gripping means can engage said valve and slide said valve as said moveable support is moved, said linking means transmitting the movement of said moveable support to said gripping means to slide said valve.

2. The mechanism recited in claim 1 wherein said moveable support is pivotally mounted at one end to said mechanism, and engages said linking means at the other end of said moveable support whereby pivotal movement of said support is transmitted by said linking means to said gripping means.

3. The mechanism recited in claim 2 wherein said linking means comprises an arm pivotally mounted on said mechanism, said arm having an elongated slot, and wherein roller means is mounted on said other end of said moveable support, said roller means positioned in said slot for movement along the length of said slot, whereby as said support is pivoted, said roller means will move in said slot and free said linking means to pivot and move said gripping means.

4. The mechanism recited in claim 1 wherein said gripping means includes a first bracket pivotally mounted on said first bracket, and drive means actuated by the movement of said linking means to pivot said first bracket on said mechanism, and to pivot said second bracket on said first bracket, said two brackets gripping and moving said valve as they are pivoted.

5. The mechanism recited in claim 4 wherein said drive means includes a cam driveable associated with said linking means, said cam engaging said first and second brackets to pivot said brackets upon movement of said linking means.

6. The mechanism recited in claim 5 wherein said linking means comprises an arm pivotally mounted on said mechanism, said arm having an elongated slot, and wherein roller means is mounted on said other end of said moveable support, said roller means positioned in said slot for movement along the length of said slot, whereby as said support is pivoted, said roller means will move in said slot and free said linking means to pivot and move said cam.

7. The mechanism recited in claim 6 wherein said arm is fixedly secured to one end of a shaft which is rotatably mounted on said mechanism, said cam being fixedly mounted on the other end of said shaft, whereby pivotal movement of said arm on said mechanism rotates said shaft and said cam.

8. The mechanism as recited in claim 3 which further includes a shaft mounted on said mechanism for rotational movement about its axis and wherein said arm is pivotally mounted on said mechanism by being fixedly secured to one end of said shaft, said gripping means being associated with and driven by the other end of said shaft whereby the pivotal movement of said arm rotates said shaft which activates said gripping means.

9. A driver for driving a disposable fluid-pumping cassette with a slideable valve, comprising:

a door moveably mounted on said driver between first and second positions for receiving said cassette;

a valve gripping mechanism mounted on said driver moveable between first and second positions;

linking means between said door and said valve gripping means to move said valve gripping means between its two positions as said door is moved between its two positions, whereby as said door is moved, said valve gripping means will move said slideable valve between open and closed positions.

10. The driver recited in claim 9 wherein one end of said door is pivotally mounted on said driver, and the other end of said door engages said linking means whereby pivotal movement of said door between first and second positions moves said valve gripping means between first and second positions.

11. The driver recited in claim 9 wherein said valve gripping means includes a first bracket pivotally mounted on said driver, and a second bracket pivotally mounted on said first bracket, said two brackets for gripping valve on a cassette therebetween, said two brackets being positioned in relation to said door such that when a cassette is being mounted on said driver, the valve will engage said first bracket as said door is moved before said second bracket engages and grips the valve between said two brackets.

12. The driver recited in claim 11 further including cam means driven by said linking means, said cam means driveably engaging said first and second brackets as said door is moved between its two positions.

13. The driver recited in claim 11 wherein said cam means includes a cam rotatably mounted on said driver, and a drive pin extending from said cam, said cam having cam surfaces which driveably engage said first bracket, said drive pin driveably engaging said second bracket.

* * * * *